(12) United States Patent
Mann et al.

(10) Patent No.: US 10,617,798 B2
(45) Date of Patent: Apr. 14, 2020

(54) DEVICE FOR ASPIRATING AND TRANSFERRING BLOOD

(71) Applicant: MEDELA HOLDING AG, Baar (CH)

(72) Inventors: Robin Mann, Villingen-Schwenningen (DE); Martin Walti, Zurich (CH)

(73) Assignee: MEDELA HOLDING AG, Baar (CH)

( * ) Notice: Subject to any disclaimer, the term of this patent is extended or adjusted under 35 U.S.C. 154(b) by 522 days.

(21) Appl. No.: 15/318,644

(22) PCT Filed: Jun. 18, 2015

(86) PCT No.: PCT/EP2015/063714
§ 371 (c)(1),
(2) Date: Dec. 13, 2016

(87) PCT Pub. No.: WO2015/197463
PCT Pub. Date: Dec. 30, 2015

(65) Prior Publication Data
US 2017/0128637 A1 May 11, 2017

(30) Foreign Application Priority Data
Jun. 26, 2014 (EP) ..................................... 14174598

(51) Int. Cl.
*A61M 1/00* (2006.01)
*A61M 1/36* (2006.01)
(Continued)

(52) U.S. Cl.
CPC ........ *A61M 1/0005* (2013.01); *A61M 1/0001* (2013.01); *A61M 1/0025* (2014.02);
(Continued)

(58) Field of Classification Search
CPC . A61M 1/0007; A61M 1/3632; A61M 1/3666
See application file for complete search history.

(56) References Cited

U.S. PATENT DOCUMENTS 3,191,600 A 6/1965 Everett
3,585,995 A 6/1971 Perkins et al.
(Continued)

FOREIGN PATENT DOCUMENTS

CN 102858388 A 1/2013
EP 131116 A1 1/1985
(Continued)

OTHER PUBLICATIONS

International Search Report and Written Opinion for Application No. PCT/EP2015/063714 dated Jun. 18, 2015.

*Primary Examiner* — Adam Marcetich
*Assistant Examiner* — Jessica R Arble
(74) *Attorney, Agent, or Firm* — Marshall, Gerstein & Borun LLP

(57) ABSTRACT

A device for aspirating and transferring blood during a surgical operation has a first chamber and a second chamber for collecting and transferring the aspirated blood, and an electronically controlled valve unit for connecting the chambers to a vacuum source. The valve unit establishes this connection alternately between the first chamber and the vacuum source and the second chamber and the vacuum source, such that the first or second chamber connected to the vacuum source can be filled with aspirated blood, and the other, second or first chamber can be emptied at the same time. The valve unit is connected to the first and second chamber and permits a pressure increase in the first or second chamber to be emptied. This device allows blood to be efficiently collected and transferred during operations in a way that is gentle on the blood.

14 Claims, 10 Drawing Sheets

(51) Int. Cl.
*A61M 39/22* (2006.01)
*A61M 39/24* (2006.01)

(52) U.S. Cl.
CPC ........ *A61M 1/0068* (2014.02); *A61M 1/3632* (2014.02); *A61M 1/3666* (2013.01); *A61M 39/223* (2013.01); *A61M 39/24* (2013.01); *A61M 2205/3306* (2013.01); *A61M 2205/3337* (2013.01)

(56) References Cited

U.S. PATENT DOCUMENTS

| | | | |
|---|---|---|---|
| 3,799,702 | A | 3/1974 | Weishaar |
| 3,896,733 | A * | 7/1975 | Rosenberg .............. A61M 1/02 604/6.1 |
| 4,846,800 | A * | 7/1989 | Ouriel ................. A61M 1/3627 604/6.15 |
| 4,923,438 | A * | 5/1990 | Vasconcellos ...... A61M 1/3627 604/319 |
| 5,586,085 | A * | 12/1996 | Lichte ................. G01F 23/2962 367/165 |
| 5,931,646 | A * | 8/1999 | Nogawa .............. A61M 1/3621 417/384 |
| 6,342,048 | B1 | 1/2002 | Verkaart et al. |
| 6,908,446 | B2 * | 6/2005 | Yokoyama .......... A61M 1/3627 210/259 |
| 7,048,727 | B1 * | 5/2006 | Moss .................. A61J 15/0003 604/27 |
| 7,981,280 | B2 * | 7/2011 | Carr ........................ A61M 1/16 210/134 |
| 8,361,042 | B1 * | 1/2013 | Gonzalez ............ A61M 1/0001 604/317 |
| 2003/0138349 | A1 * | 7/2003 | Robinson ................ A61M 1/02 422/44 |
| 2003/0144646 | A1 | 7/2003 | Se et al. |
| 2008/0058695 | A1 * | 3/2008 | Perovitch ............ A61M 1/0001 604/6.03 |
| 2009/0187132 | A1 * | 7/2009 | Ishida ........................ A61J 1/05 604/6.11 |
| 2011/0247620 | A1 * | 10/2011 | Armstrong ........... B01D 53/047 128/204.23 |
| 2014/0074017 | A1 * | 3/2014 | Gao .................. A61M 5/16831 604/28 |

FOREIGN PATENT DOCUMENTS

| | | |
|---|---|---|
| EP | 2080529 A1 | 7/2009 |
| EP | 2191858 A1 | 6/2010 |
| EP | 2380611 A1 | 10/2011 |
| EP | 2468324 A1 | 6/2012 |
| JP | 3-207372 | 9/1991 |
| JP | 5-103832 | 4/1993 |
| JP | 2003-28098 A | 1/2003 |
| JP | 2013/524920 A | 6/2013 |
| JP | 2014-504906 A | 2/2014 |
| WO | WO-9820957 A1 | 5/1998 |
| WO | WO-2011/132122 A2 | 10/2011 |
| WO | WO-2012/076632 A1 | 6/2012 |

* cited by examiner

DEVICE FOR ASPIRATING AND TRANSFERRING BLOOD

CROSS-REFERENCE TO RELATED APPLICATIONS

The present application is the US national phase of International Patent Application No. PCT/EP2015/063714, filed Jun. 18, 2015, which application claims priority to European Application No. EP 14174598.4, filed Jun. 26, 2014. The priority application, EP14174598.4, is hereby incorporated by reference.

TECHNICAL FIELD

The present invention relates to a device for aspirating and transferring blood during a surgical operation, and to a secretion collection container.

PRIOR ART

During or after surgical operations in which the patient loses a large amount of blood, it has for years been customary to return autologous blood almost simultaneously to the patient. In mechanical autotransfusion, blood that is aspirated during the operation is collected outside the body, usually cleaned and transfused back to the patient. Particularly when using a heart-lung machine, this mechanical autotransfusion is employed in order to aspirate blood from the surgical wound and likewise to return blood to the blood circulation of the patient.

Peristaltic pumps are commonly used to transport the blood in this extracorporeal circulation. U.S. Pat. No. 6,517,512 discloses a roller pump for use with a heart-lung machine, wherein the pump switches on and off automatically depending on a liquid detector signal. Other autotransfusion appliances with roller pumps are known, for example, from U.S. Pat. No. 3,799,702 or EP 1 131 116.

US 2003/0144646 proposes emptying an intermediate container of an autotransfusion appliance by means of overpressure and delivery to a heart-lung machine. It is proposed to use a roller pump to generate this overpressure.

It is known that the sensitive blood cells are often damaged in the extracorporeal circulation and, consequently, can no longer be returned to the patient. It is true that damaged cells can be filtered out. However, this is an elaborate procedure. Hose pumps or roller pumps damage the blood cells mechanically, since the blood is conveyed by squeezing of the hose. Moreover, in the event of large pressure differences, the cell membranes of the red blood cells detach. Therefore, in U.S. Pat. No. 6,342,048, an electronically controlled piston pump is proposed, of which the underpressure is varied in accordance with the amount of blood that accumulates in the surgical wound and is to be aspirated. The reinfusion of the collected blood into the circuit of the heart-lung machine takes place, as before, via a roller pump.

Since a patient can lose several litres of blood from the surgical wound, it is necessary to return the aspirated blood relatively quickly to the blood circuit. In doing so, however, the wound must not be exposed to too great an underpressure. As has already been mentioned above, a rapid change of pressure when emptying the blood collection container must also be avoided. U.S. Pat. No. 3,896,733 therefore proposes using two blood collection containers, which are alternately filled and emptied again. The change-over between the two containers can take place manually, or automatically by means of a photoelectric filling level sensor. One container is filled by means of underpressure, while the other container is ventilated in order to deliver the blood as quickly as possible to the heart-lung machine.

U.S. Pat. No. 3,585,995 describes a blood collection container with two chambers, of which the inlets and outlets can be controlled alternately by valves.

Moreover, EP 2 080 529 discloses a combined reservoir with two areas separate from each other.

U.S. Pat. No. 3,191,600 proposes the use of two blood collection containers, each of them with two chambers, wherein the content of the upper chambers is emptied into the chambers lying underneath.

U.S. Pat. No. 4,846,800 describes an autotransfusion appliance with a blood collection container which has two chambers that are alternately filled and emptied. If the outlets of the chambers are located in the lower area of the collection container, ventilation valves are provided in order to cancel the underpressure in the chamber that is to be emptied. If the outlets of the chambers are located in the upper area of the collection container, the chambers are emptied by application of an overpressure. If the outlets are arranged at the top, they are formed by the upper ends of ascending pipes.

Although autotransfusion has already been in use for many years, there are no available appliances that can be used flexibly and that also function optimally in emergency situations, i.e. when an unexpectedly large amount of blood occurs in the surgical wound. Moreover, the known appliances scarcely take account of the circumstances prevailing in an operating theatre. The known autotransfusion appliances and in particular their blood collection containers have to be arranged as close as possible to the reservoir of the heart-lung machine, and the blood collection containers have to be arranged above this reservoir.

DISCLOSURE OF THE INVENTION

It is therefore an object of the invention to make available a device for aspirating and transferring blood during a surgical operation, which device allows blood to be efficiently and flexibly apirated and transferred in a way that is gentle on the blood.

In order to achieve this object, the present invention provides a device for aspirating and transferring blood during a surgical operation which has a first chamber and a second chamber for collecting and transferring the aspirated blood, and an electronically controlled valve unit for connecting the chambers to a vacuum source. The valve unit establishes this connection alternately between the first chamber and the vacuum source and between the second chamber and the vacuum source, such that the first or second chamber connected to the vacuum source can be filled with aspirated blood, and the other, second or first chamber can be emptied at the same time. The valve unit is connected to the first and second chamber and permits a pressure increase in the first or second chamber to be emptied. By virtue of the valve unit, the pressure increase is caused electronically and/or controlled electronically.

The valve unit can, for example, comprise a four-way valve which creates the connection to the vacuum source and also permits the pressure increase. In another embodiment, the valve unit has a first valve module which establishes the connection between the chambers and the vacuum source, and a second valve module, which permits the pressure increase.

The device according to the invention can, for example, be an autotransfusion appliance for returning autologous blood to the patient or it can be part of such an appliance. In particular, it can be part of a heart-lung machine or can be integrated into the extracorporeal circuit of such a machine.

The device according to the invention has the advantage that gentle aspiration of the blood is ensured by virtue of the vacuum source. The controllable valve unit ensures that the chamber to be emptied can be emptied quickly and efficiently.

The two valve modules are preferably controlled independently of each other, such that one chamber can also be filled without the other one having to be emptied throughout the filling time, or one chamber can be emptied without the other one having to be filled throughout the emptying time. This is advantageous since the blood in the surgical wound often occurs in quantities that vary over time. The independent nature of the control of the two valve modules can be limited by safety measures.

Preferably, the valve unit is connectable to an overpressure source, wherein it creates an alternate connection between the first chamber and the overpressure source and the second chamber and the overpressure source. In this way, the first or second chamber to be emptied can be emptied with a pressure higher than atmospheric pressure. This has the advantage that the emptying procedure is accelerated. It can therefore last a much shorter time than the filling procedure. This is particularly advantageous if the heart-lung machine has an increased blood requirement and/or if a relatively large amount of blood for aspiration occurs in the surgical wound.

The use of an overpressure source moreover has the advantage that the device according to the invention can be arranged in the operating theatre independently of the site of the heart-lung machine. Its blood collection container can also lie deeper than the reservoir of the heart-lung machine. Moreover, the hose connections to the patient and also to the reservoir of the heart-lung machine can be relatively long. By virtue of the overpressure, it is always ensured that the chamber is emptied quickly and completely. This also allows blood to be withdrawn uninterrupted from the patient.

Preferably, a first filling level sensor for measuring the filling level in the first chamber and a second filling level sensor for measuring the filling level in the second chamber are present, wherein the valve unit and in particular the two valve modules are controlled according to at least one of these sensor signals. This permits fully automatic control of the valve unit and in particular of the two valve modules.

Preferably, the appliance is designed as a compact appliance and thus saves space in the operating theatre. For this purpose, the valve unit and in particular the first and second valve modules are arranged in a housing. Preferably, the first and second chambers are held releasably in a fixed position on the housing. The compactness and operability of the device are improved if the first and second chambers are arranged in a common blood collection container, which is held releasably in a fixed position on the housing. Preferably, the vacuum source and/or the overpressure source are also arranged in the housing. Preferably, a control unit for controlling the valve unit is also arranged in the housing.

In one embodiment, the vacuum source and the overpressure source are two separate pumps. In another embodiment, they are formed by a single pump, for example by the exhaust of the vacuum pump being used as overpressure source.

The vacuum source and/or the overpressure source are non-peristaltic pumps, preferably piston pumps and more preferably diaphragm pumps. They are preferably controllable pumps, in particular pumps driven by an electric motor.

It is also possible to use more than two chambers, in which case the valve unit then preferably operates the first, second and third or subsequent chamber in succession.

In a preferred embodiment, the chambers are designed such that they permit a reliable measurement even with a low filling level. This can be achieved, for example, by the fact that their interior has a downwardly tapering internal cross section. As filling level sensors, it is possible to use known sensors such as optical or optoelectronic sensors. If a capacitive sensor is used, it preferably extends from an upper area of the chamber down into the tapering area.

Collection chambers of this kind can also be used in other fields and not only for the collection of blood. A corresponding container is thus regarded here as an additional invention. For example, such a container with one chamber or with two or more chambers can be correspondingly used in medical drainage, e.g. thorax drainage, wound drainage or liposuction. For this reason, the container is designated below in part as a secretion collection container and not as a blood collection container, but the description given here of the nature of the container applies in each case to both types of containers.

BRIEF DESCRIPTION OF THE DRAWINGS

Preferred embodiments of the invention are described below with reference to the drawings, which serve only for illustration and are not to be interpreted as limiting the invention. In the drawings.

In the figures, same parts are provided with same reference signs.

DESCRIPTION OF PREFERRED EMBODIMENTS

Figure 1:
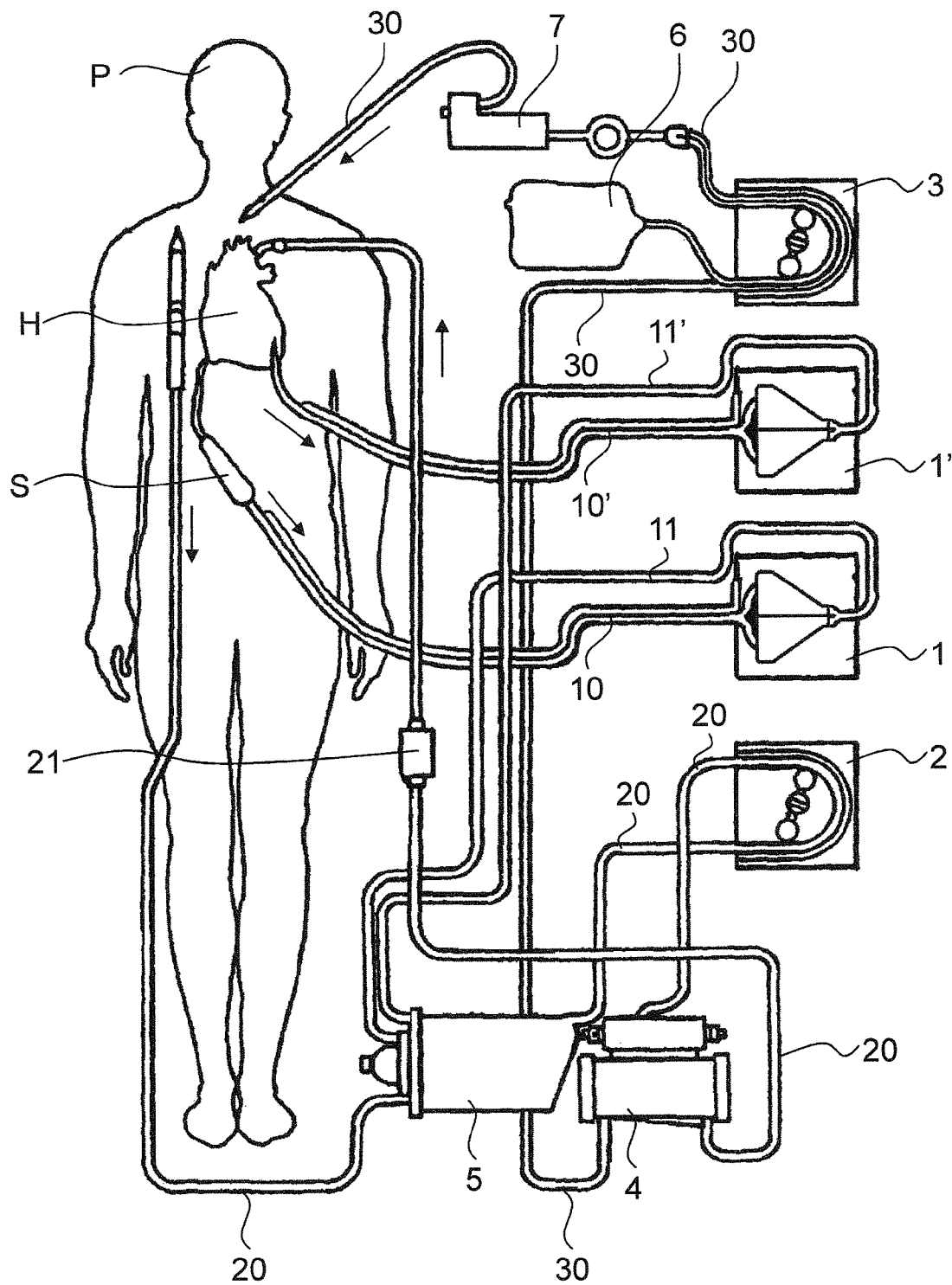
FIG. 1 shows a schematic view of a patient with a first heart-lung machine and the device according to the invention.

FIG. 1 shows a patient P with an extracorporeal blood circuit by means of a heart-lung machine. His heart is designated in the figure by H, and an open surgical wound by S. The direction of flow of the blood is shown by arrows.

The heart-lung machine is composed mainly of
a hose system 20, which forms an extracorporeal circuit,
a reservoir 5 which is located in the hose system 20 and in which the blood is collected,
a centrifugal pump or first peristaltic pump 2 which is arranged downstream of the reservoir 5 in the hose system 20 and which acts on an area of the hose system 20 and thus transports the blood located therein,
an oxygenator 4, which is arranged downstream of the pump 2 in the hose system 20 and which provides the blood with sufficient oxygen saturation before the blood is then returned via one or more filters 21 to the vascular system of the patient P.

If the heart H of the patient P is stopped, a second peristaltic pump 3 with a delivery line 30 is then normally used. This second pump 3 conveys blood from the oxygenator 4 to the patient P via a heat exchanger 7. A cardioplegic solution from a solution container 6 of the heart-lung machine is admixed to the blood.

Other known systems can also be employed as heart-lung machine, and for stopping the heart, and can be used together with the device according to the invention described below. Moreover, the device according to the invention described below can also be used without heart-lung machine. In this case, it customarily has additional elements for reconditioning the blood before the latter is returned to the human body.

The device according to the invention is described below:

The blood gathering in the operating site S is in this example returned to the patient P by means of autotransfusion. For this purpose, a first suction line 10 on the patient side leads to a first autotransfusion appliance 1 according to the invention. From this appliance 1, a first transfer line 11 leads to the reservoir 5 of the heart-lung machine.

Depending on the size of the surgical wound or on the nature of the operation, further autotransfusion appliances can be used. In FIG. 1, a second appliance 1' according to the invention is shown with a corresponding suction line 10' from the patient P to the appliance and a transfer line 11' from the appliance 1' into the reservoir 5.

Figure 2:
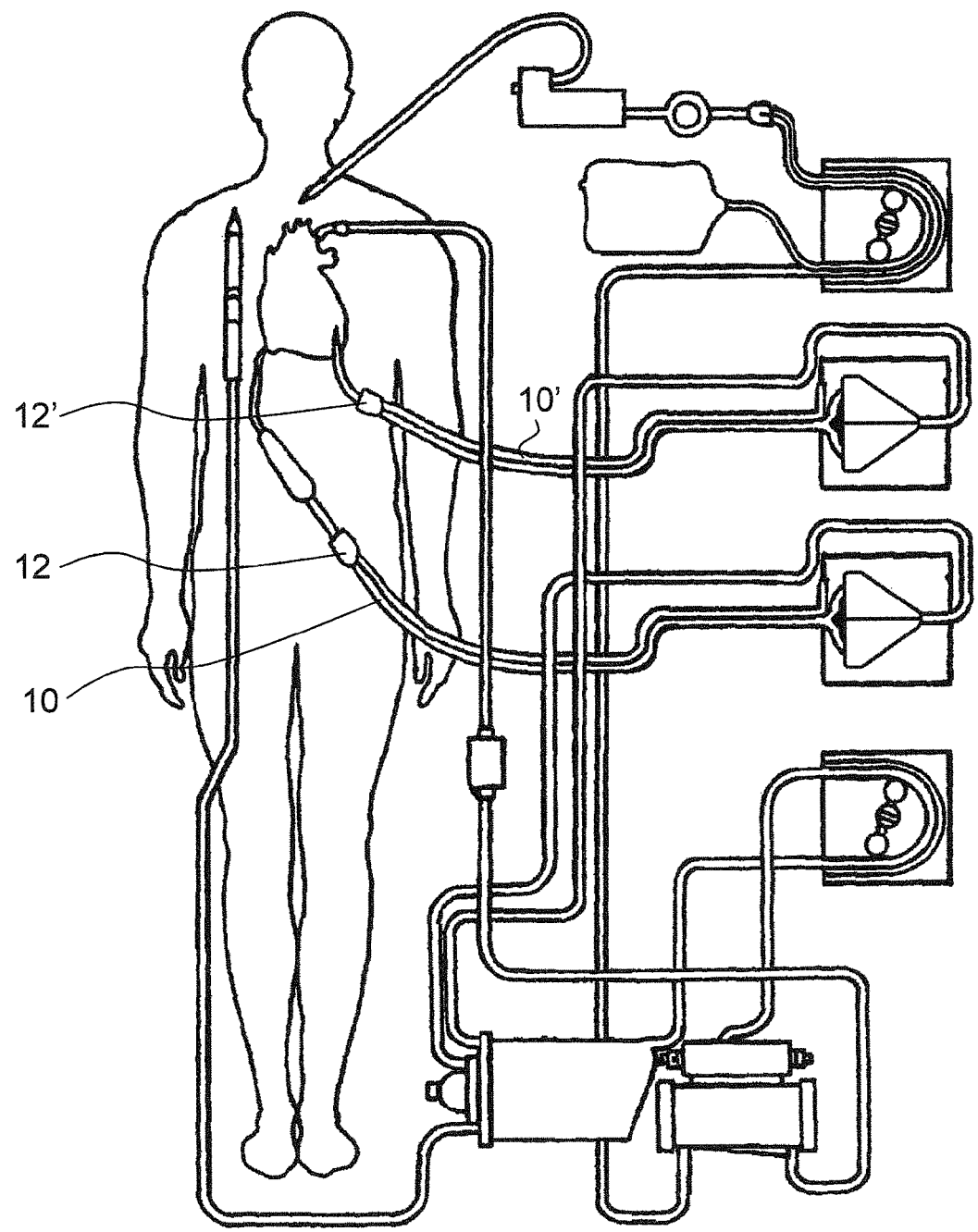
FIG. 2 shows a schematic view of a patient with a second heart-lung machine and the device according to the invention.

The illustrative embodiment according to FIG. 2 is practically identical to that of FIG. 1, except that here an overpressure valve 12, 12' for protecting the patient P is present in each of the two suction hoses 10, 10' on the patient side.

Figure 3:
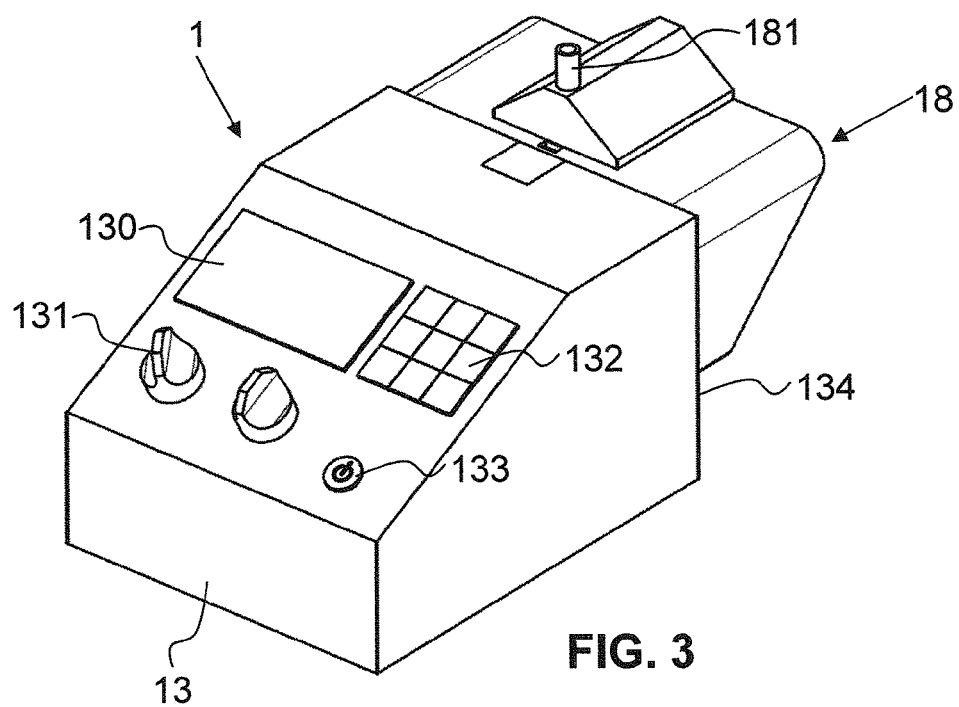
FIG. 3 shows a perspective view of a device according to the invention in a first embodiment.

FIG. 3 shows an autotransfusion appliance 1 according to the invention and a device according to the invention as part of such an appliance. The latter has a housing 13 and a blood collection container 18 held releasably thereon.

Display means and actuation means are present on the housing 13, for example a screen 130, actuation buttons 131, actuation keys 132, and an on/off switch 133.

The blood collection container 18 is preferably arranged on a side, here the rear face 134, of the housing 13. It has a patient-side port 181 for connection to the patient-side suction line 10. Moreover, a transfer-side port for connection to the transfer line 11 is present, although it is not visible in FIG. 3 since, in this illustrative embodiment, it is located on the underside of the container 18.

Figure 4:
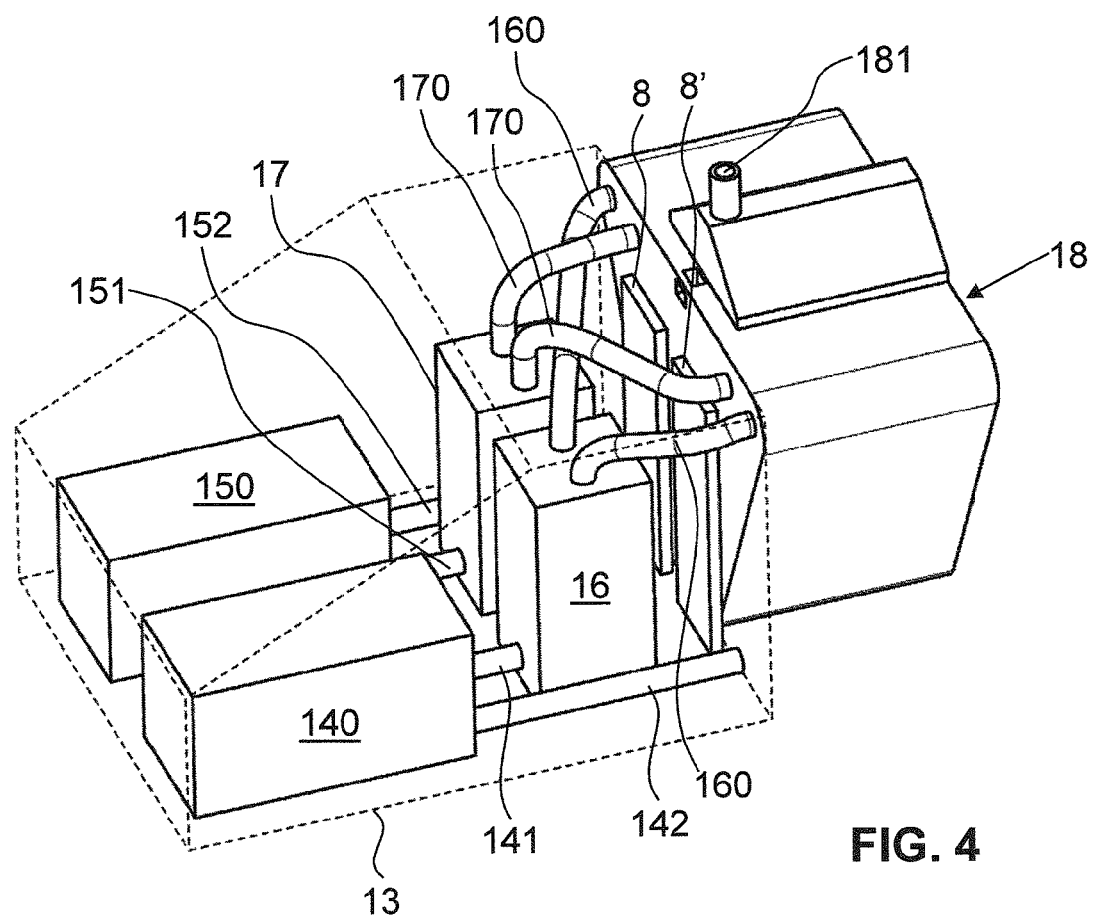
FIG. 4 shows a schematic view of the interior of a housing of the device according to FIG. 3.

As can be seen in FIG. 4, the housing 13 accommodates a vacuum or underpressure pump 140 with an associated first valve module 16, an overpressure pump 150 with an associated second valve module 17, and various lines. The two valve modules 16, 17 form a valve unit. Instead of two independent modules separate from each other, it is also possible to use a valve unit with a single module, the latter being, for example, a four-way valve.

A first connection line 141 connects the vacuum pump 140 to the first valve module 16, an exhaust line 142 connects the vacuum pump 140 to the outlet side of the housing 13. From the first valve module 16, two separate vacuum lines 160 lead to outlet openings in the rear wall 134 of the housing 13. These outlet openings are sealingly connectable or connected to first connector openings 180 (see FIG. 10) of the blood collection container 18.

A second connection line 151 connects the overpressure pump 150 to the second valve module 17, an aspiration line 152 connects the overpressure pump 150 to the outside of the housing 13. From the second valve module 17, two separate overpressure lines 170 lead to two outlet openings in the rear wall 134 of the housing 13. These outlet openings are sealingly connectable or connected to second connector openings 180' (see FIG. 10) of the blood collection container 18.

Filling level sensors 8, 8' are arranged on the rear wall 134 of the housing or alternatively on the blood collection container 18. They are preferably capacitive filling level sensors. They preferably extend from the underside of the container 18 to a maximum admissible filling height.

Figure 5:
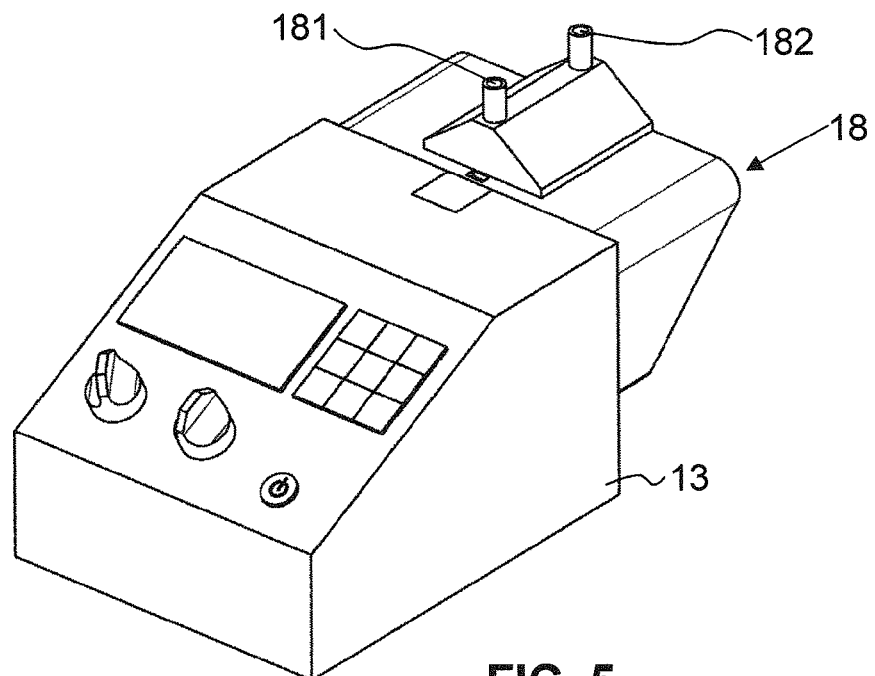
FIG. 5 shows a perspective view of a device according to the invention in a second embodiment.
Figure 6:
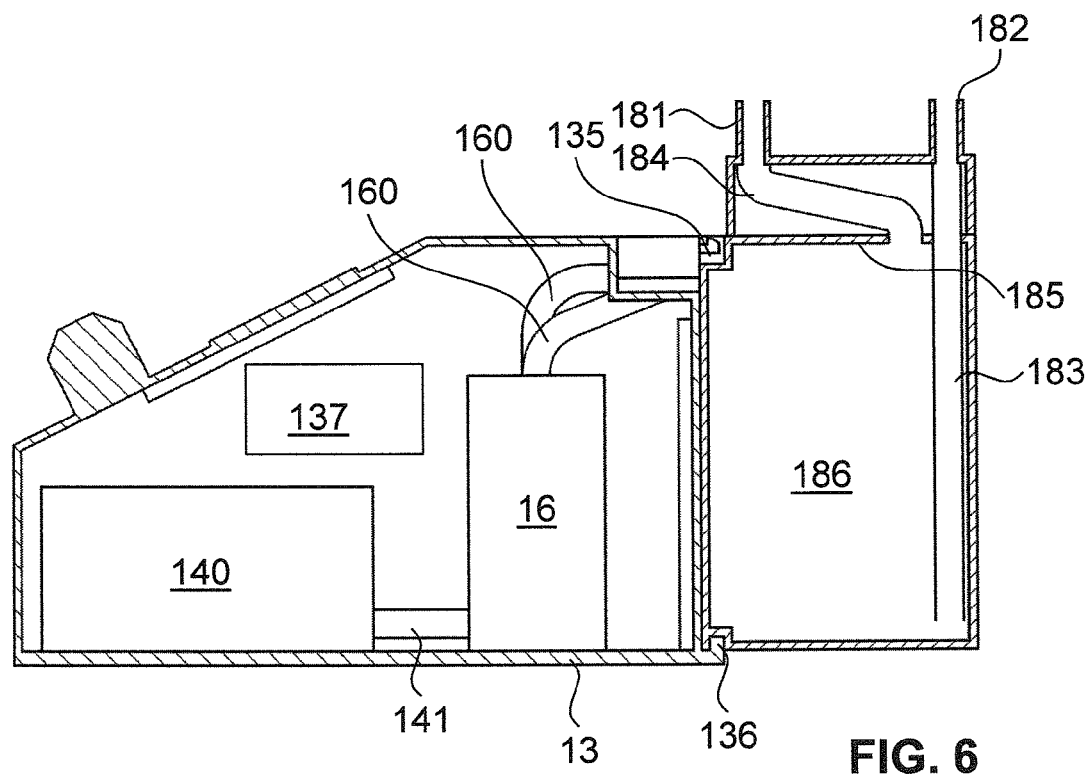
FIG. 6 shows a longitudinal section through the device according to FIG. 5.

FIGS. 5 and 6 show a second embodiment of the device according to the invention. It differs from the first illustrative embodiment in that the patient-side port 181 and the transfer-side port 182 are both arranged on the top of the blood collection container 18. The transfer-side port 182 merges into an ascending pipe or an ascending line 183, which extends into the lower area of a blood collection chamber 186. The patient-side port 181 is likewise connected to this chamber 186, for example via a connecting channel or a connecting hose 184. Preferably, a horizontally extending separating rib otherwise separates the area of the ports 181, 182 from the chamber 186 and has only two through-openings for said connections. This avoids blood sloshing or spraying back into the suction line 10 or into the transfer line 11.

FIG. 6 also shows a variant of how the container 18 can be held releasably on the housing 13. In this example, it can be latched into place, by means of latching elements 135, 136 on the upper and lower sides of the container 18 and of the housing 13 being able to be brought into engagement with each other.

FIGS. 7 to 10 show a preferred embodiment of a blood collection container 18 according to the invention with two chambers 186, 186'. The container 18 is preferably in one piece. It is preferably made of a plastic. It is preferably transparent. It is preferably designed as a disposable product and is discarded after the surgical operation.

On its top face, the container 18 has the patient-side port 181 and the transfer-side port 182. Otherwise, the container 18 has a mirror symmetrical configuration. From the patient-side port 181, the branching connection line 184 having a Y shape leads into the interior of the container. From the transfer-side port 182, a Y-shaped branch leads into two ascending pipes 183, which reach into the lower area of the interior of the container.

The interior of the container 18 is divided into two areas, which are preferably completely separate from each other. In this example, they are located next to each other and are separated from each other by a separating wall 189. One of said connection lines 184 and one of said ascending pipes 183 lead in each case into one of the areas. One area is described below. The other area is of identical construction.

The area is basically formed by a blood collection chamber 186 which, in its upper area, is delimited by an oblique rib 187. Starting from the separating wall 189, this oblique rib 187 extends down towards the opposite side and in so doing it extends almost but not quite completely over the full width of the chamber. In the direction perpendicular thereto, the oblique rib 187 extends over the entire length of the area or of the chamber 186. The ascending pipe 183 passes through the oblique rib 187.

Arranged in the area above the oblique rib 187 is the upwardly curved separating rib 185, which extends over the entire length of the area and defines a pump-side area. This area is connected to the rest of the interior only by a narrow upper gap. In this area, the first and second connector openings 180, 180' are arranged, which serve for connection to the vacuum line 160 or the overpressure line 170, respectively. These connector openings 180, 180' are provided with filters 188. These filters are known in the prior art. Other filters can also be present at other locations, as is likewise known from the prior art. These filters serve to protect the appliance.

The separating rib 185 prevents blood from spraying onto the filters and closing them early. Moreover, it forms a further protection for the pumps. The oblique rib 187 prevents the aspirated blood from sloshing back into the suction line and additionally allows aspirated blood to flow down via the oblique rib 187 into the collection chamber 186.

The chamber 186 has a downwardly tapering cross section. Preferably, the surface area in the lowermost region of the chamber 186 is at most half the surface area in the upper region, i.e. in the region just below the lower end of the oblique rib 187. This permits a relatively precise measurement of the filling level even with small filling quantities, particularly when capacitive filling level sensors are used for this purpose.

Figure 7:
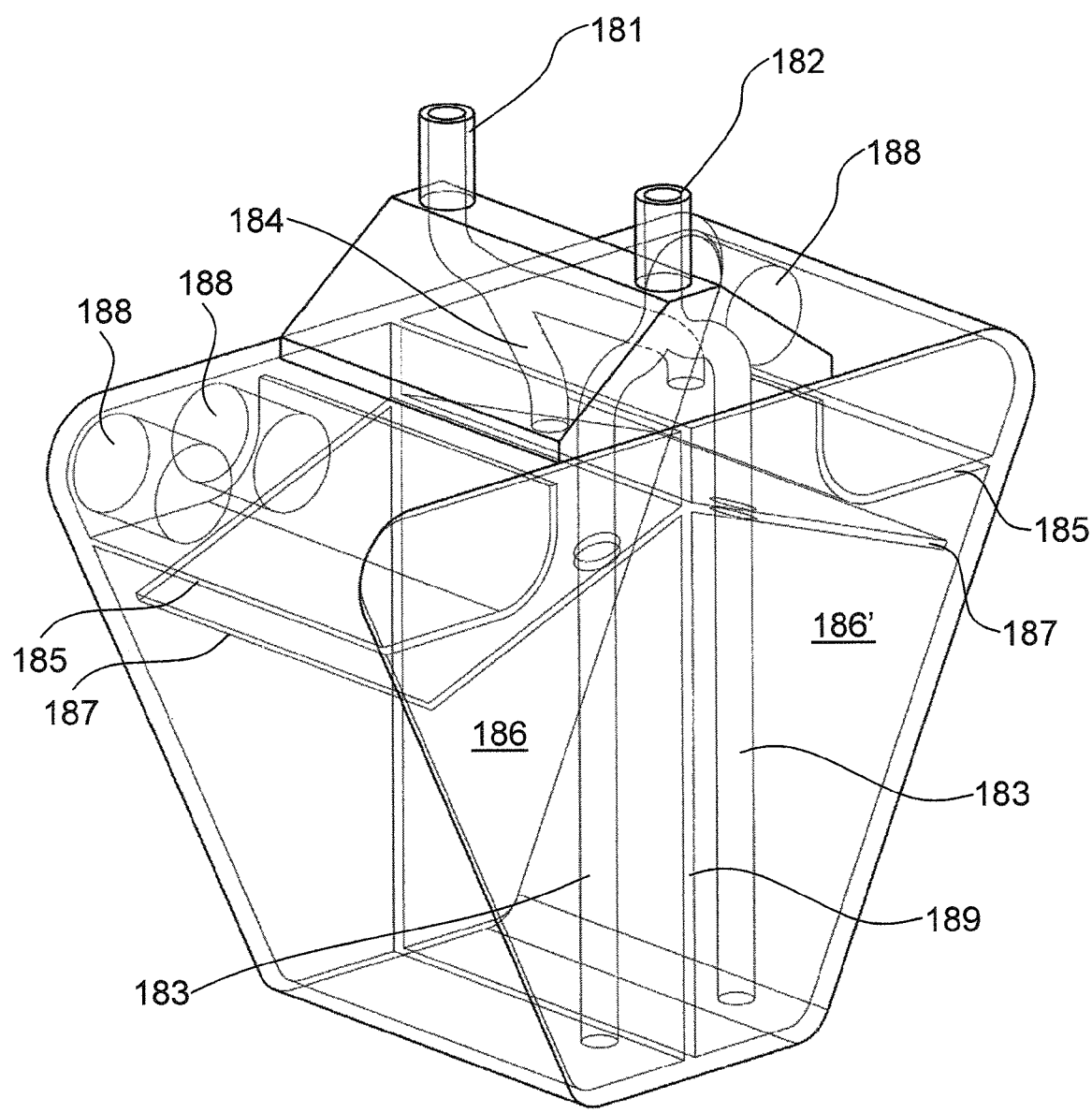
FIG. 7 shows a perspective view of a secretion collection container according to the invention in a first embodiment, with the interior made visible.
Figure 8:
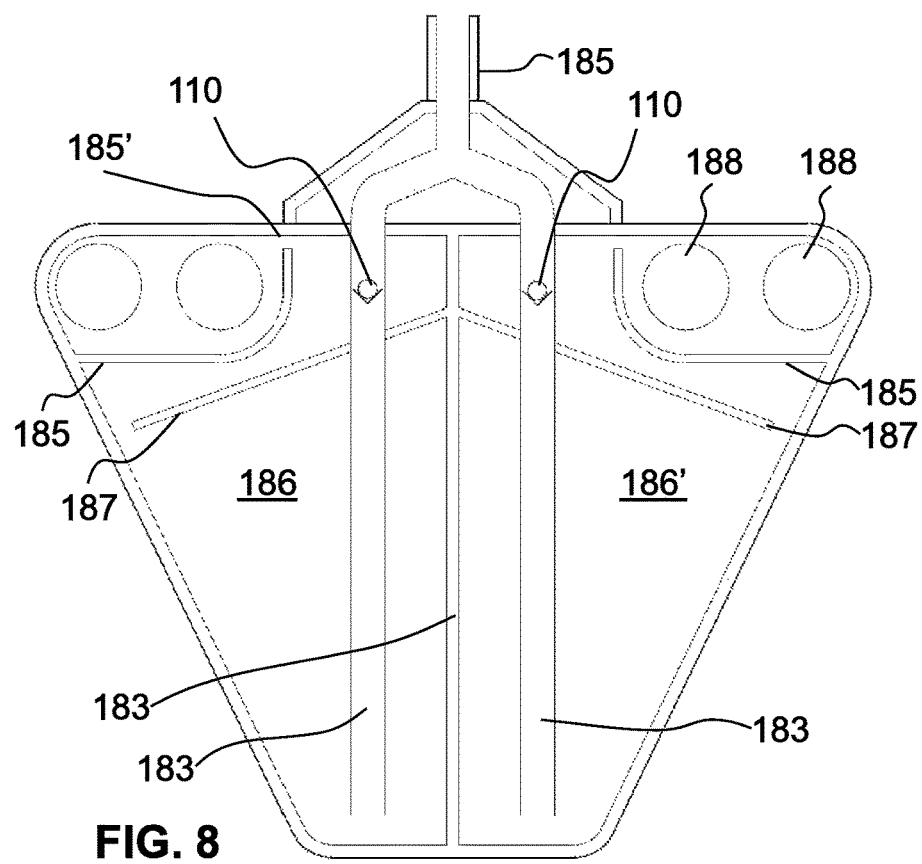
FIG. 8 shows a first longitudinal section through the secretion collection container according to FIG. 7.

Preferably, the blood collection container 18 therefore has a rectangular base area, but two mutually opposite trapezoidal side walls and two oblique walls connecting these trapezoidal side walls, and a substantially rectangular upper wall, as can be seen clearly in FIGS. 7 and 8. All the walls are preferably substantially plane. Preferably, only the two mutually opposite side walls are oblique, and the other walls extend in the vertical or horizontal direction.

The two chambers 186 of the container 18 can be filled and emptied alternately. That is to say, when one chamber is being filled, the other can at the same time be emptied. Emptying takes place at the latest when the corresponding filling level sensor 8, 8' of a control unit 137 of the appliance 1 indicates that the corresponding chamber 186 is full.

Figure 9:
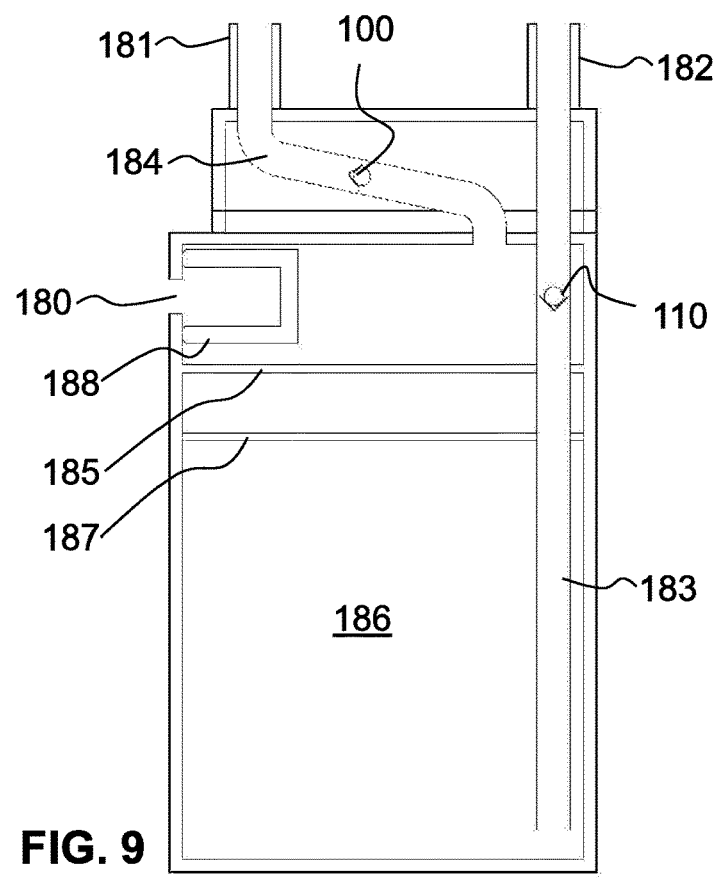
FIG. 9 shows a second longitudinal section through the secretion collection container according to FIG. 7.
Figure 10:
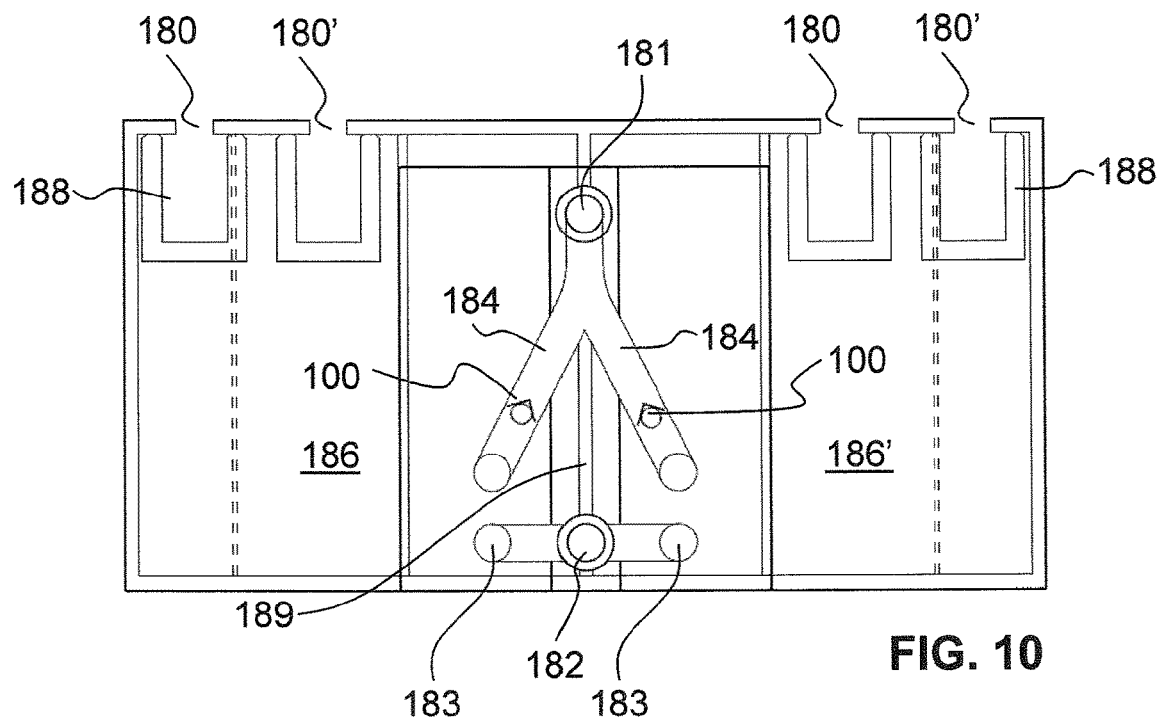
FIG. 10 shows a cross section through the secretion collection container according to FIG. 7.

One-way valves 100 are accordingly present which open and close the connection between the suction line 10 and the collection chamber 186. These valves can be controlled by the control unit or can close at a predetermined pressure. As is shown in FIGS. 9 and 10, they can be part of the blood collection container 18, or they can also be arranged in the area of the suction line 10 or at the patient-side port 181.

Moreover, one-way valves 110 are present which open and close the connection between the collection chamber 86 and the transfer line 11. These valves can likewise be controlled by the control unit or can close at a predetermined pressure. As is shown in FIGS. 8 and 9, they can also be part of the blood collection container 18, or they can also be arranged in the area of the transfer line 11 or at the transfer-side port 182.

The one-way valves can be simple non-return valves, for example, or they can likewise be controlled by the control unit 137.

Figure 11:
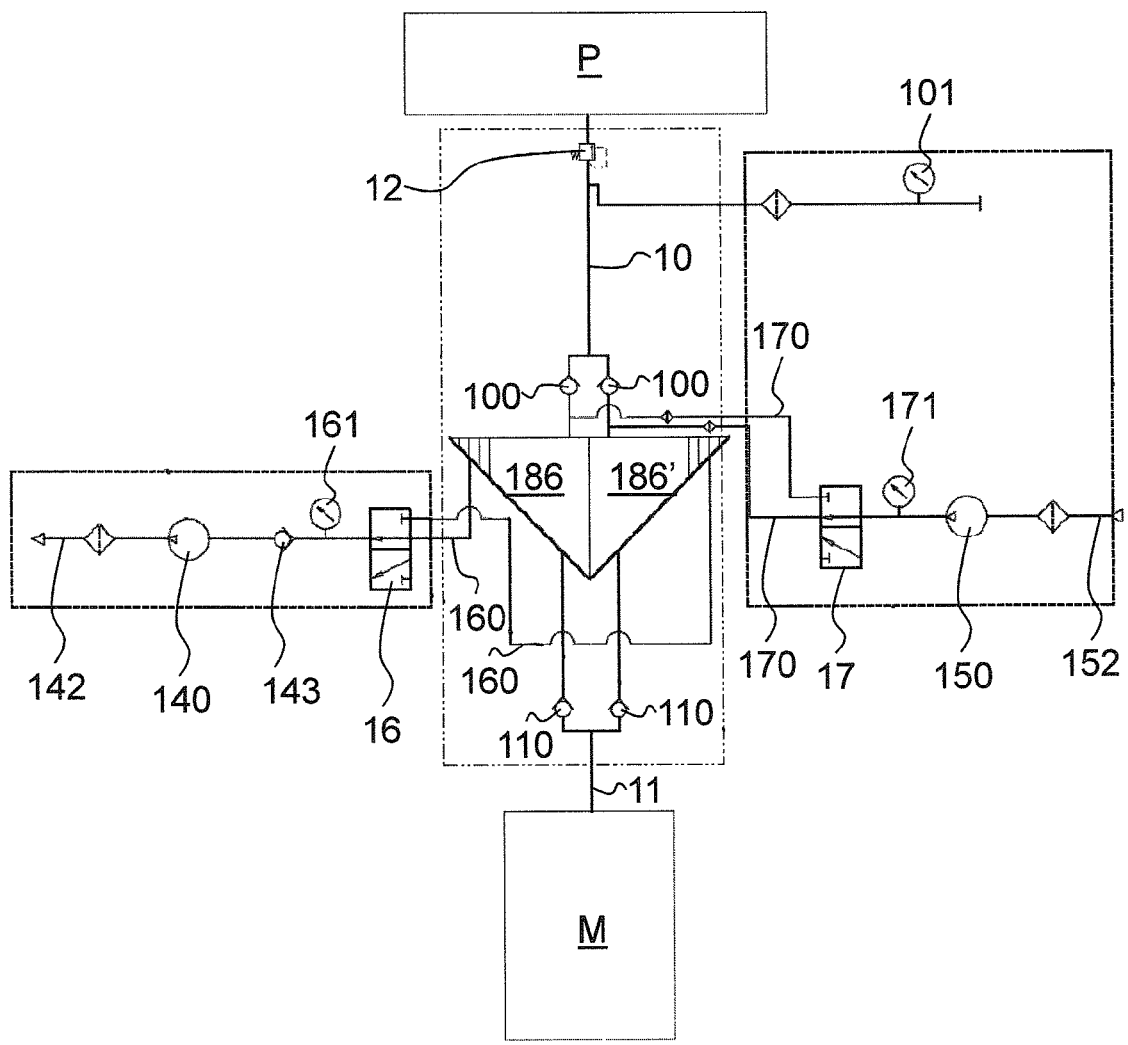
FIG. 11 shows a circuit diagram of a variant of the device according to FIG. 3.

The mode of operation of this appliance 1 is now described with reference to FIG. 11. The patient P is attached to a heart-lung machine M, wherein moreover an autotransfusion takes place by means of the appliance according to the invention.

The vacuum pump 140 is alternately connectable to one of the two collection chambers 186 via the first valve module 16. If it is connected to the left-hand chamber 186, its connection to the right-hand chamber 186 is interrupted, as is shown here. An underpressure is thus generated in the left-hand chamber 186 and the blood is aspirated into the left-hand chamber 186 when the left-hand patient-side valve 100 is opened. The left-hand transfer-side valve 110 is closed in the process.

The right-hand chamber 186 which is filled with blood can simultaneously be emptied and can deliver the collected blood to the heart-lung machine via the transfer line 11. For this purpose, the right-hand chamber 186 is connected by means of the second valve module 17 to the overpressure pump 150, of which the connection to the left-hand chamber 186 is at the same time interrupted. When the right-hand patient-side valve 100 is closed, the right-hand chamber 186 is subject to an overpressure, i.e. a pressure above atmospheric pressure, wherein the blood can flow off by virtue of the right-hand transfer-side valve 110 being opened.

The patient is additionally protected from harm by the preferable presence of an overpressure valve 12 in the suction hose 10. Preferably, a pressure sensor 101 moreover monitors the pressure in the suction line. This pressure sensor 101 is preferably likewise part of the appliance 1 according to the invention, and it is preferably connected to the control of the appliance 1, in particular to the control of the overpressure pump 150. For this purpose, a double-lumen hose is preferably used, wherein one lumen serves as suction line and the second lumen serves as measurement line. A hose of this kind is shown in FIGS. 1 and 2. Systems of this kind are known from the field of medical drainage. Alternatively or in addition, the measurement line can serve as a flushing line, in order to free the hose from blockages or to deliver a medical solution to the patient.

If the left-hand chamber 186 is filled, a change-over is made, i.e. the right-hand chamber 186 is now subjected to underpressure and the left-hand chamber empties by virtue of overpressure.

The vacuum pump 140 and the overpressure pump 150 are non-peristaltic pumps. They are preferably piston pumps and more preferably vacuum diaphragm pumps. These can be controlled and regulated very precisely. The non-return valve 143 serves to maintain the vacuum, even if the vacuum pump 140 is intermittently switched off. Pressure sensors or manometers 161, 171 are preferably present in order to monitor the pressure generated in the respective pump and, depending on the embodiment, also to control said pressure.

Figure 12:
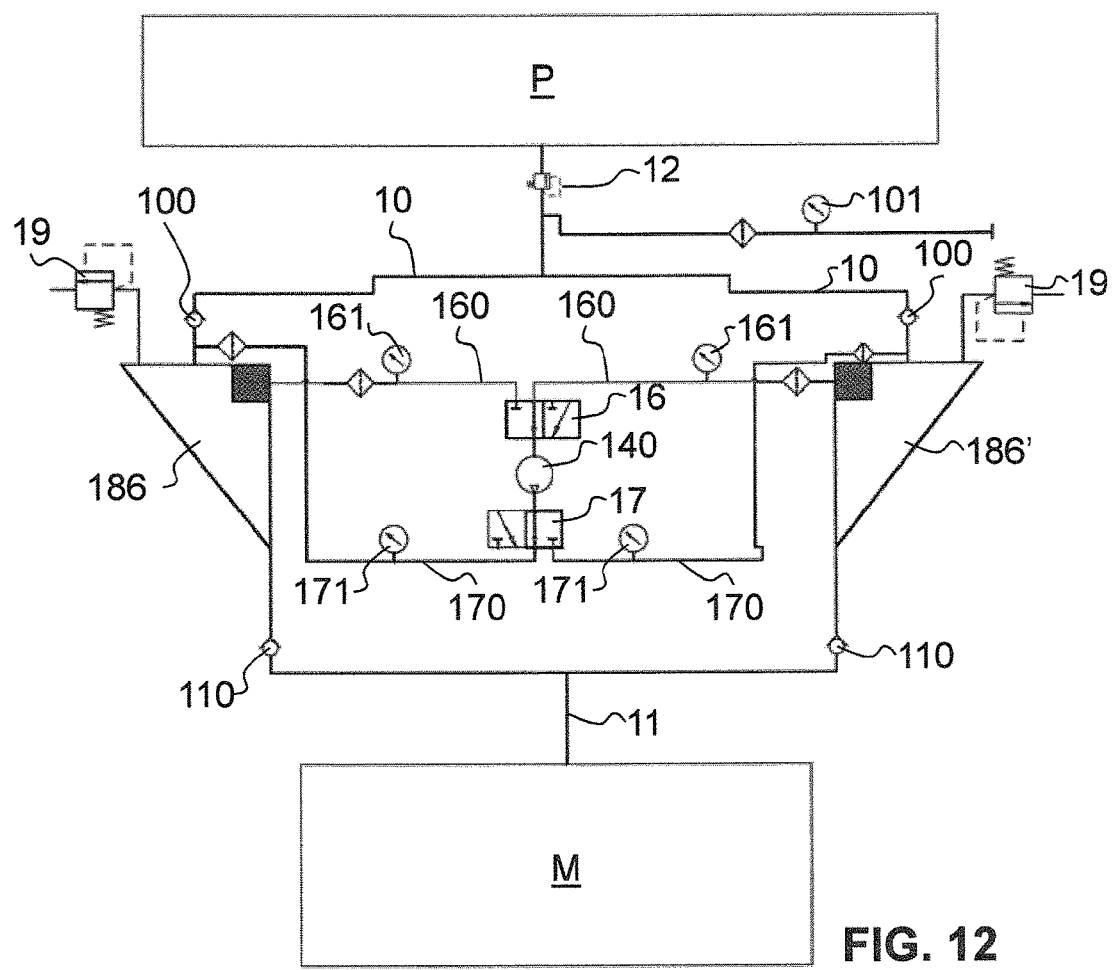
FIG. 12 shows a circuit diagram of the device according to the invention in a second embodiment.

FIG. 12 shows a variant of the appliance according to the invention. Here, a single pump 140 serves both as vacuum pump and also as overpressure pump. The function of overpressure pump is achieved by using the exhaust as overpressure line and therefore attaching this to the second valve module 17. In this example, the two chambers 186 are moreover provided with overpressure valves 19, which open when there is too high an overpressure in the respective chamber 186. These overpressure valves 19 can also be used in the other illustrative embodiments.

Figure 13:
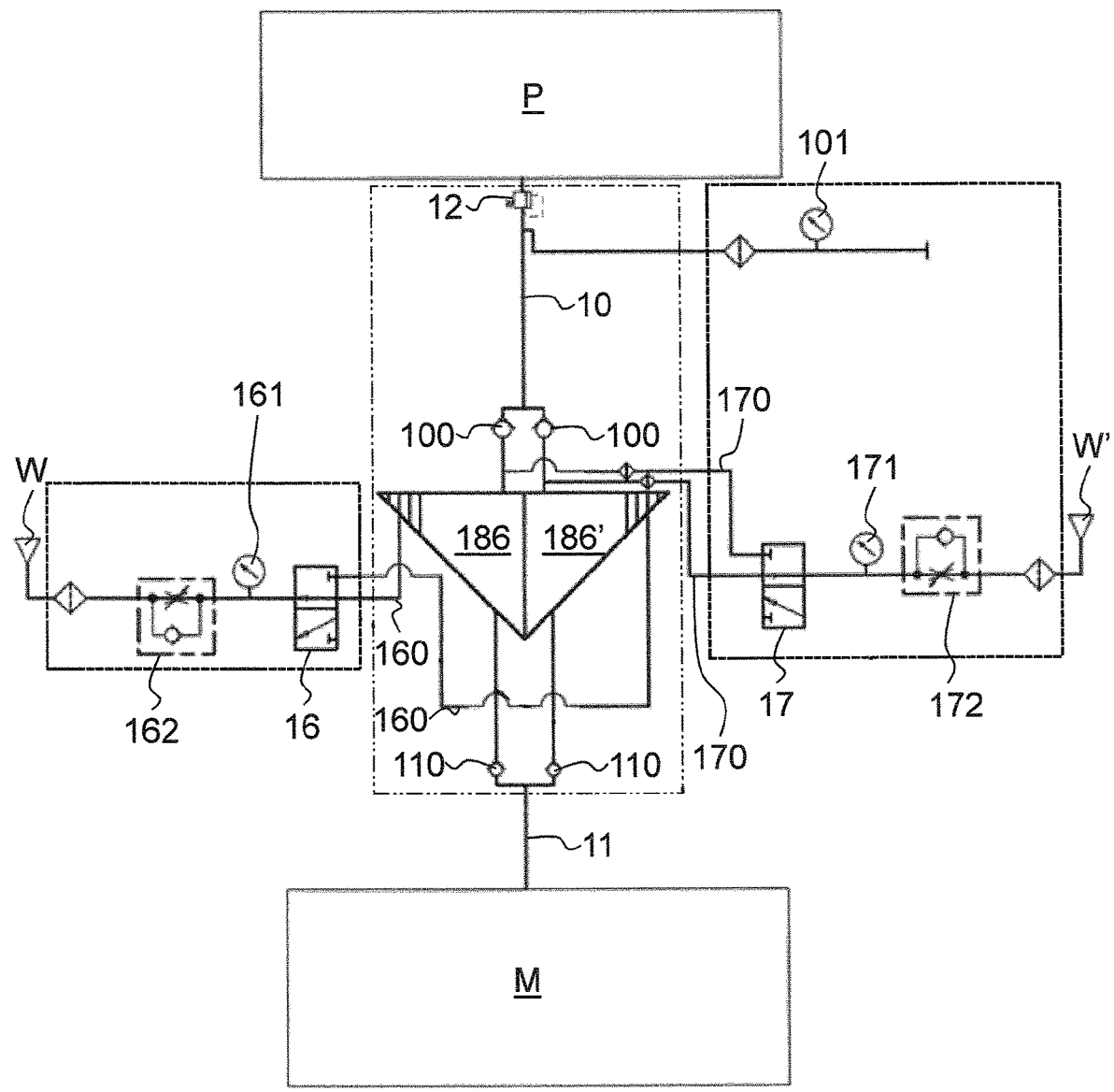
FIG. 13 shows a circuit diagram of the device according to the invention in a third embodiment.

In the variant according to FIG. 13, the appliance 1 itself has no pumps, and instead it can be connected to wall attachments W, W' of the hospital in order thereby to be attached to a vacuum source and to an overpressure source. Corresponding inlet valves 162, 172 are present in order to open and close the connection to the corresponding suction source.

Figure 14:
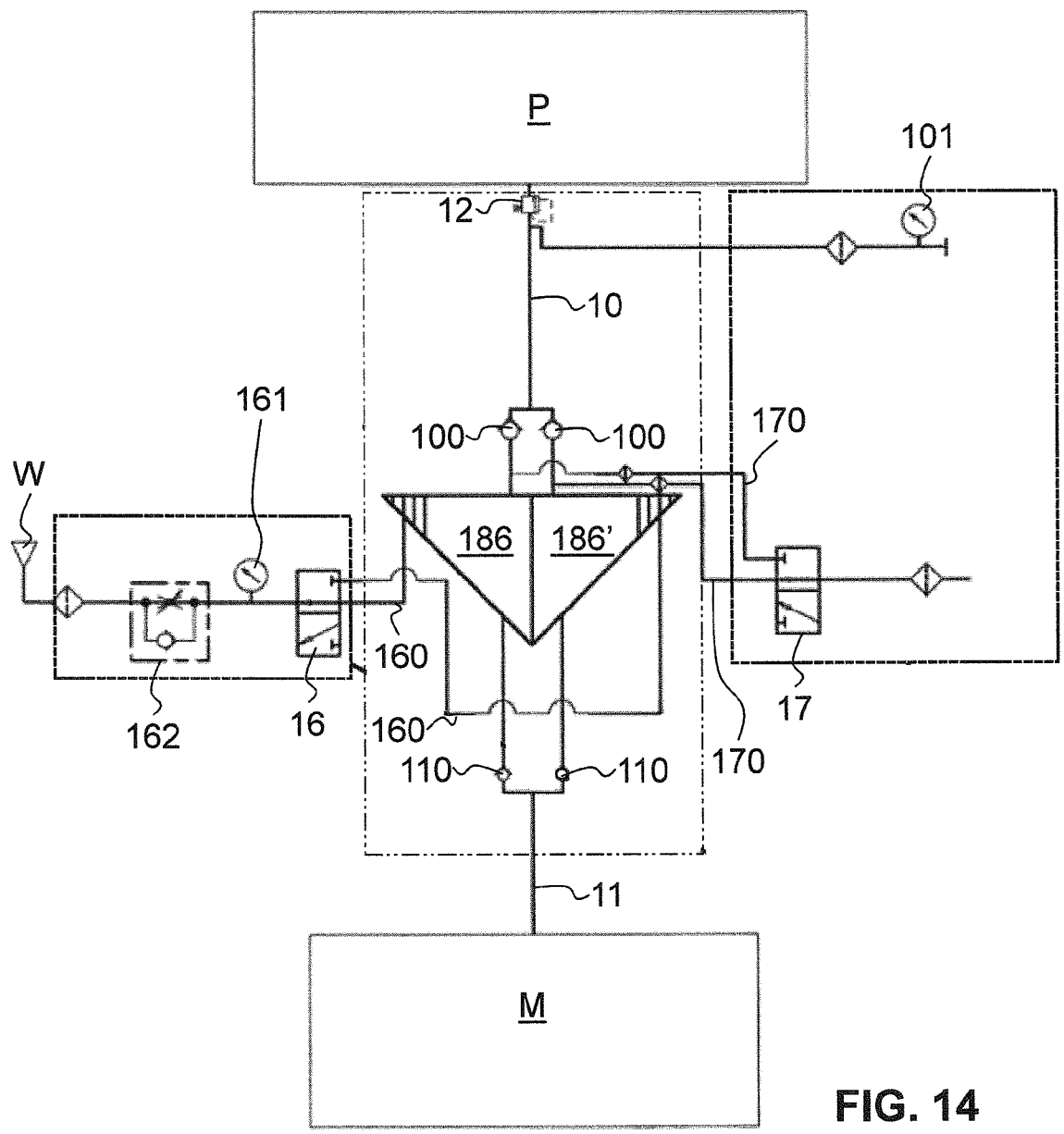
FIG. 14 shows a circuit diagram of the device according to the invention in a fourth embodiment.

In the embodiment according to FIG. 14, only a wall attachment W is present for the vacuum source. The drainage side is merely ventilated, i.e. the filled chamber 186 is brought to atmospheric pressure in order to be emptied.

The appliance according to the invention allows blood to be efficiently collected and transferred during operations in a way that is gentle on the blood. The secretion collection container according to the invention permits increased precision in the detection of the filling level.

What is claimed is:

1. A device for aspirating and transferring blood during a surgical operation, comprising:
    a first chamber and a second chamber for collecting and transferring the aspirated blood, and an electronically controlled valve unit for connecting the chambers to a vacuum source,
    wherein the valve unit establishes this connection alternately between the first chamber and the vacuum source and between the second chamber and the vacuum source, such that the first or the second chamber connected to the vacuum source can be filled with aspirated blood, and the other, second or first chamber can be emptied at the same time,
    wherein the valve unit is connected to the first and second chamber and permits a pressure increase in the first or the second chamber to be emptied,
    wherein the valve unit has a first valve module which establishes the connection between the first and second chamber and the vacuum source and has an additional second valve module, which permits the pressure increase,
    and wherein the first and second valve modules are controllable independently of each other.

2. The device according to claim 1, wherein the valve unit is connectable to an overpressure source and creates an alternate connection between the first chamber and the overpressure source, such that the first or second chamber to be emptied can be emptied with a pressure higher than atmospheric pressure.

3. The device according to claim 1, wherein a first filling level sensor for measuring the filling level in the first chamber and a second filling level sensor for measuring the filling level in the second chamber are present, wherein the valve unit is controlled according to a sensor signal from at least one of these filling level sensors.

4. The device according to claim 1, wherein the valve unit is arranged in a housing, wherein the first and second chambers are held releasably in a fixed position on the housing.

5. The device according to claim 4, wherein the first and second chambers are arranged in a common blood collection container, which is held releasably in a fixed position on the housing.

6. The device according to claim 4, wherein the vacuum source is arranged in the housing.

7. The device according to claim 4, wherein a control unit for controlling the valve unit is arranged in the housing.

8. The device according to claim 2, wherein the vacuum source and the overpressure source are two separate pumps, or wherein the vacuum source and the overpressure source are formed by a single pump.

9. The device according to claim 1, wherein the vacuum source is a non-peristaltic pump.

10. The device according to claim 1, wherein the vacuum source is a controllable pump.

11. The device according to claim 1, wherein the chambers have a downwardly tapering internal cross section.

12. The device according to claim 3, wherein the filling level sensor of each chamber extends from the top downward into the area of the tapering internal cross section.

13. A secretion collection container having a first chamber and a second chamber for collecting and transferring aspirated blood during a surgical operation, comprising
    an inlet,
    an outlet, and
    at least one interior,
    wherein the interior is divided, by means of a separating wall, into a first area and a second area,
    wherein the first area basically forms the first chamber and the second area basically forms the second chamber,
    wherein the interior has a downwardly tapering internal cross section, and
    wherein the first chamber and the second chamber are, in a respective upper area, delimited by an oblique rib.

14. The device according to claim 9, wherein the vacuum source is a piston pump or a diaphragm pump.

* * * * *